US010543383B2

(12) United States Patent
Kase

(10) Patent No.: US 10,543,383 B2
(45) Date of Patent: Jan. 28, 2020

(54) MEDICAL INSTRUMENT AND ULTRASONIC SURGICAL APPARATUS

(71) Applicant: OLYMPUS CORPORATION, Hachioji-shi, Tokyo (JP)

(72) Inventor: Seigo Kase, Sagamahara (JP)

(73) Assignee: OLYMPUS CORPORATION, Tokyo (JP)

( * ) Notice: Subject to any disclaimer, the term of this patent is extended or adjusted under 35 U.S.C. 154(b) by 198 days.

(21) Appl. No.: 15/842,081

(22) Filed: Dec. 14, 2017

(65) Prior Publication Data

US 2018/0117365 A1 May 3, 2018

Related U.S. Application Data

(63) Continuation of application No. PCT/JP2016/067095, filed on Jun. 8, 2016.

(30) Foreign Application Priority Data

Jun. 17, 2015 (JP) ................................ 2015-122223

(51) Int. Cl.
*A61N 7/02* (2006.01)
*A61B 17/32* (2006.01)
(Continued)

(52) U.S. Cl.
CPC ........ *A61N 7/02* (2013.01); *A61B 17/320092* (2013.01); *A61B 18/1442* (2013.01);
(Continued)

(58) Field of Classification Search
CPC ............ A61B 17/320092; A61B 17/32; A61B 2017/320093; A61B 2017/320095;
(Continued)

(56) References Cited

U.S. PATENT DOCUMENTS 10,136,942 B1 * 11/2018 Cosman, Jr. ....... A61B 18/1477
2011/0196403 A1 8/2011 Robertson et al.
(Continued)

FOREIGN PATENT DOCUMENTS

CN 102781352 A 11/2012
CN 103889355 A 6/2014
(Continued)

OTHER PUBLICATIONS

Dec. 19, 2017 International Preliminary Report on Patentability issued in International Patent Application No. PCT/JP2016/067095.
(Continued)

*Primary Examiner* — Christopher L Templeton
*Assistant Examiner* — Chima U Igboko
(74) *Attorney, Agent, or Firm* — Oliff PLC

(57) ABSTRACT

A medical instrument includes: a rod including a curving portion formed on a distal side of an extension along a longitudinal axis and curved with respect to the longitudinal axis; and a sheath including an inner peripheral surface and a cutout, the cutout formed in at least one of a distal portion and a proximal portion of the sheath, the sheath configured to insert the rod along a central axis extending and defined from the distal portion to the proximal portion and to protrude the curving portion from an opening of the inner peripheral surface in the distal portion.

14 Claims, 9 Drawing Sheets

(51) Int. Cl.
*A61B 18/14* (2006.01)
*A61B 17/00* (2006.01)
*A61B 18/00* (2006.01)

(52) U.S. Cl.
CPC ............... *A61B 2017/00853* (2013.01); *A61B 2017/320093* (2017.08); *A61B 2017/320094* (2017.08); *A61B 2017/320095* (2017.08); *A61B 2018/0063* (2013.01); *A61B 2018/00083* (2013.01); *A61B 2018/00404* (2013.01); *A61B 2018/00589* (2013.01); *A61B 2018/00601* (2013.01); *A61B 2018/00607* (2013.01); *A61B 2018/00958* (2013.01); *A61B 2018/00994* (2013.01)

(58) Field of Classification Search
CPC ......... A61B 2017/320094; A61B 2017/00853; A61B 18/1442; A61B 2018/00083; A61B 2018/00404; A61B 2018/00589; A61B 2018/00601; A61B 2018/00607; A61B 2018/0063; A61B 2018/00958; A61B 2018/00994; A61N 7/02
See application file for complete search history.

(56) References Cited

U.S. PATENT DOCUMENTS

| | | |
|---|---|---|
| 2012/0238946 A1 | 9/2012 | Nita et al. |
| 2013/0030949 A1 | 1/2013 | Sundaresan |
| 2013/0303949 A1 | 11/2013 | Kawaguchi et al. |

FOREIGN PATENT DOCUMENTS

| | | |
|---|---|---|
| JP | H10-05237 A | 1/1998 |
| JP | 2013-519441 A | 5/2013 |
| JP | 2014-121618 A | 7/2014 |

OTHER PUBLICATIONS

Jan. 31, 2017 Office Action issued in Japanese Patent Application No. JP 2016-572607.
Sep. 6, 2016 International Search Report issued in International Patent Application No. PCT/JP2016/067095.
Jan. 3, 2019 Extended Search Report issued in European Patent Application No. 16811521.0.
Aug. 1, 2019 Office Action issued in Chinese Patent Application No. 201680021970.7.

* cited by examiner

MEDICAL INSTRUMENT AND ULTRASONIC SURGICAL APPARATUS

CROSS-REFERENCE TO RELATED APPLICATIONS

This application is a Continuation Application of PCT Application No. PCT/JP2016/067095, filed Jun. 8, 2016 and based upon and claiming the benefit of priority from prior Japanese Patent Application No. 2015-122223, filed Jun. 17, 2015, the entire contents of all of which are incorporated herein by reference.

BACKGROUND OF THE INVENTION

1. Field of the Invention

This invention relates to a medical instrument and an ultrasonic surgical apparatus.

2. Description of the Related Art

For example, US 2013/0303949 A1 discloses a medical instrument which may transmit vibration to a rod having a curving portion whose distal portion is bent in one direction. A rigid sheath made of an electrically insulating material is disposed on the outside of the rod.

BRIEF SUMMARY OF THE INVENTION

According to an aspect of the present invention, there is provide a medical instrument comprising: a rod including an extension which extends along a longitudinal axis; and a curving portion which is formed on a distal side of the extension and which is curved with respect to the longitudinal axis; and a sheath including an inner peripheral surface and a cutout which are formed by integral molding, the inner peripheral surface having an inside diameter larger than a distance between a distal end of the curving portion and the extension and smaller than a distance between the distal end of the curving portion and a part of the curving portion, the cutout being formed in at least one of a distal portion and a proximal portion of the sheath, the sheath being configured to insert the rod along a central axis extending and defined from the distal portion to the proximal portion and to protrude the curving portion from an opening of the inner peripheral surface in the distal portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

Initially, the first embodiment is described with reference to FIG. 1 to FIG. 5.

Figure 1:
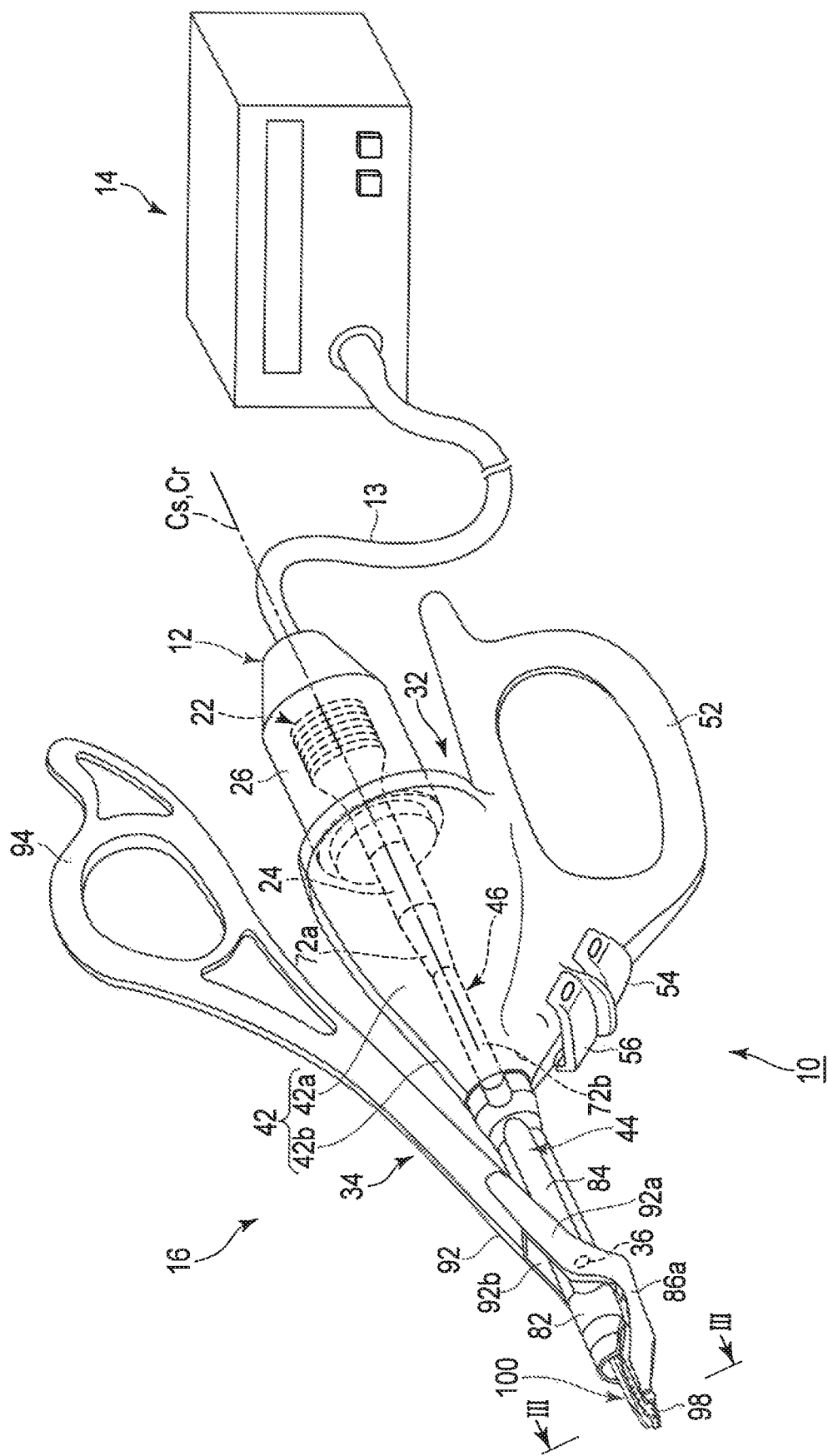
FIG. 1 is a schematic diagram showing an ultrasonic surgical apparatus according to first to six embodiments.

As shown in FIG. 1, an ultrasonic surgical apparatus 10 which is a medical apparatus according to the first embodiment of the present invention includes an ultrasonic transducer unit 12, an output controller 14 to which the ultrasonic transducer unit 12 is connected, and a treatment instrument (medical instrument) 16 to which a distal portion of the ultrasonic transducer unit 12 is coupled so that an ultrasonic treatment can be conducted. In response to the operation of later-described switches 54 and 56, the output controller 14 can supply at least one of energy for ultrasonic output and energy for high-frequency output to the treatment instrument 15 through the ultrasonic transducer unit 12.

The ultrasonic transducer unit 12 is connected to the output controller 14 via a cable 13. The ultrasonic transducer unit 12 includes an ultrasonic transducer 22 which vibrates in accordance with the output of the output controller 14, a vibration transmission body 24 which is connected to the ultrasonic transducer 22 and which transmits the vibration generated in the ultrasonic transducer 22, and a cover 26 which covers the ultrasonic transducer 22 and the vibration transmission body 24 and which is connected to a proximal portion of the treatment instrument 16.

The treatment instrument 16 is forceps-shaped (scissors-shaped) The treatment instrument 16 includes a treatment instrument main body 32, a clamp arm 34, and a shaft 36 which pivotally supports the clamp arm 34 swingably (turnably) on the treatment instrument main body 32. The longitudinal direction of the shaft 36 is preferably orthogonal to a central axis Cs of a second sheath 64.

Figure 2A:
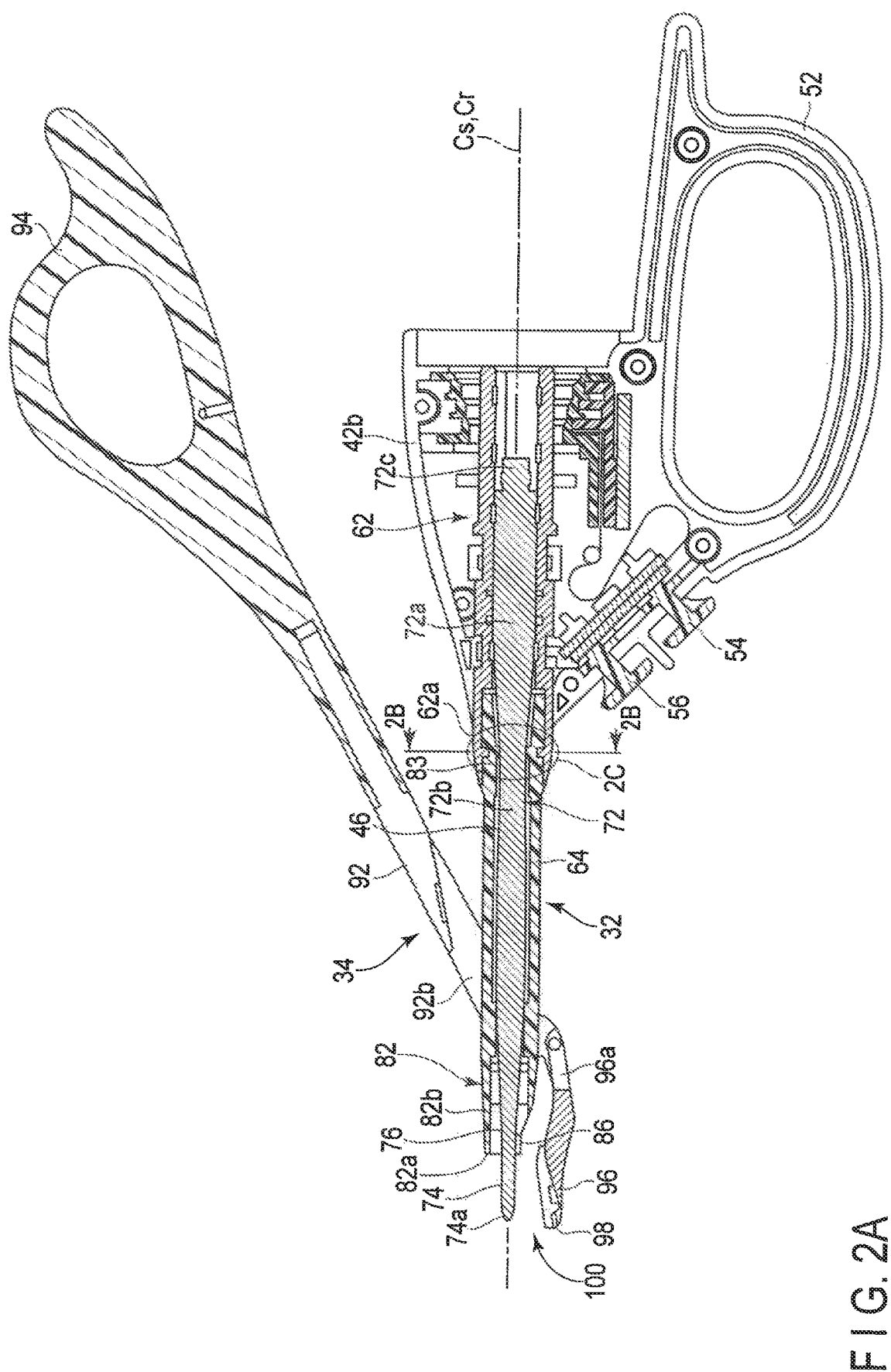
FIG. 2A is a schematic longitudinal sectional view taken along the line 2A-2A in FIG. 2E, showing a treatment instrument of the ultrasonic surgical apparatus according to the first to six embodiments.

For example, as shown in FIG. 1 and FIG. 2A, the treatment instrument main body 32 includes a substantially conical housing 42, a sheath 44 held on the housing 42, and a rod (waveguide) 46 inserted in the sheath 44. The rod 46 can transmit vibration generated in the ultrasonic transducer 22 to the vibration transmission body 24 from a proximal side to a distal side of the vibration transmission body 24.

The housing 42 is configured so that, for example, housing portions 42a and 42b comprising a pair of horizontally divided resin molds are joined to each other by snap fitting, press fitting, adhesive bonding, fusing, welding, or mechanical means The ultrasonic transducer unit 12 is removably connected to a proximal portion of the housing 42.

For example, a first finger putting portion 52 which is an annular in one example is integrally formed at a position off a central axis of the housing 42 (a central axis Cs of the second sheath 64). Two button switches 54 and 56 are provided in the vicinity of the first finger putting portion 52. These button switches 54 and 56 are provided, for example, at positions where the index finger (and the middle finger) of a surgeon can be mounted in a state in which the surgeon disposes the middle finger and the ring finger Or the ring finger and the little finger on the first finger putting portion 52.

If the button switch 54 is pressed, for example, bipolar type high-frequency output is performed in a seal mode, and a living tissue is coagulated or a blood vessel is sealed if the button switch 56 is pressed, ultrasonic output and bipolar type high-frequency output are simultaneously performed in a seal-and-cut mode, and a living tissue is coagulated or cut open, or a blood vessel is sealed or cut open. Naturally, for example, ultrasonic output alone may be performed by pressing the button switches 54 and 56. Moreover, an unshown heater may be disposed in a later-described jaw 98 so that a living tissue can be treated by heat transmission from the heater to the jaw 98.

The sheath 44 includes a first sheath (proximal-side sheath) 62 mainly inserted through the inside of the housing 42, and the second sheath (distal-side sheath) 64 which is coupled to a distal portion of the first sheath 62 and then extends to the outside of the housing 42. The first sheath 62 is formed into a substantially circular cylindrical shape. The first sheath 62 may be integrally formed, or may be circular-cylindrically shaped by two half-pipe-shaped divided bodies which are combined by a suitable connection structure such as fitting. The second sheath 64 is integrally molded by a single cylindrical member having a substantially circular cylindrical shape. For example, a distal portion 62a of the first sheath 62 and a proximal portion 83 of the second sheath 64 are coupled to each other by a suitable coupling structure, for example, fitted or screwed together, and constitute the long sheath 44.

The waveguide rod 46 made of a metallic material such as a titanium alloy material having high vibration transmitting properties and having electric conductivity is provided inside the sheath 44.

The rod 46 includes an extension 72 which accounts for most of the length of the rod 46 and which extends straight, and a curving portion (treatment region) 74 which is formed on the distal side of the extension 72 and which is curved with respect to a later-described central axis (longitudinal axis) Cr. The extension 72 includes, on its proximal side, a diameter changing portion 72a which decreases in the outside diameter toward the distal side, and a constant diameter portion 72b which is formed on the distal side of the diameter changing portion 72a and which has a constant outside diameter and which is smaller in diameter than the diameter changing portion 72a.

Figure 3:
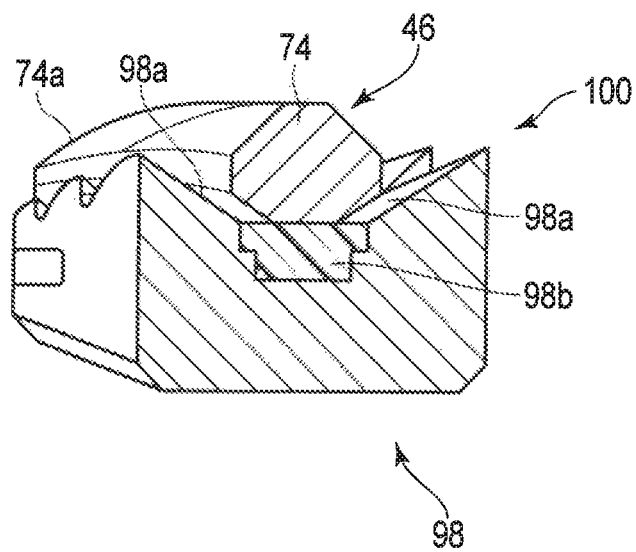
FIG. 3 is a schematic cross sectional view taken along the line III-III in FIG. 1.

The curving portion 74 of the waveguide rod 46 is bent in one direction at a curving point 76 at the distal end of the constant diameter portion 72b of the extension 72. The curving portion 74 is, for example, bent in a substantially "J"-shape with respect to the constant diameter portion. 72b of the extension 72. In the present embodiment, it is appropriate that the curving portion 74 of the waveguide rod 46 not only transmit ultrasonic vibration to a living tissue but also be used as a first electrode portion which passes a high-frequency electric current to the living tissue in cooperation with inclined surfaces (second electrode portion) 98a of a later-described jaw 98. In addition, it is appropriate that the cross section of the curving portion 74 be octagonally shaped, as shown in FIG. 3.

A connecting portion 72c which is connected to the distal end of the vibration transmission body 24 of the ultrasonic transducer unit 12 is formed at the proximal end of the diameter changing portion 72a of the extension 72 of the waveguide rod 46. The ultrasonic transducer unit 12 is coupled to the proximal portion of the housing 42 and a proximal portion of the sheath 44 (a proximal portion of the first sheath 62). In this instance, the distal end of the vibration transmission body 24 of the ultrasonic transducer unit 12 can be coupled to the connecting Portion 72c at the proximal end of the waveguide rod 46, for example, by screwing. As a result of the coupling, the vibration transmission body 24 of the ultrasonic transducer unit 12 is acoustically and electrically connected to the waveguide rod 46. The waveguide rod 46 can transmit ultrasonic vibration generated in the ultrasonic transducer unit 12, and can also apply the frequency electric current output from the output controller 14.

The entire length of the vibration transmission body 24 of the ultrasonic transducer unit 12 and the entire length of the waveguide rod 46 are suitably set by a resonant frequency output by the ultrasonic transducer 22 of the ultrasonic transducer unit 12. A coupling part between the distal end of the vibration transmission body 24 and the proximal end of the waveguide rod 46 is set to be located at an antinode position of vibration where stress on the coupling part is the lowest when the vibration is generated in the ultrasonic transducer 22. A distal end 74a of the curving portion 74 of the waveguide rod 46 is set to be located at the antinode position of vibration when the vibration is generated in the ultrasonic transducer 22.

As shown in FIG. 4A to FIG. 4E, the second sheath 64 includes a distal portion 82 having an opening 82a, and a cylindrical portion 84 formed on the proximal side of the distal portion 82. The second sheath 64 extends from the distal portion 82 to the proximal portion 83 to define the central axis Cs.

A diameter decreasing portion 82b which decreases in the outside diameter toward a distal end 64a is formed in the distal portion (a distal portion of the sheath 44) 82 of the second sheath 64. The curving portion 74 of the rod 46 remains protruding from the distal end 64a of the diameter decreasing portion 82b. The outside diameter of the diameter decreasing portion 82b is preferably tapered from the proximal side toward the distal end 64a.

A cutout (distal side cutout) 86 is formed in the distal portion 82 of the second sheath 64 at a position including the distal end 64a. A length L1 between the distal end 64a of the second sheath 64 and a proximal end 86a of the cutout 86 is adjusted, for example, by the length and shape from the distal end 74a of the curving portion 74 of the rod 46 to the curving point 76, or by the outside diameter of the rod 46. Here, the cutout 86 passes through from an inner peripheral surface 66a of the second sheath 64 to an outer peripheral surface 66b which is diametrically outwardly located with respect to the central axis Cs.

Figure 4A:
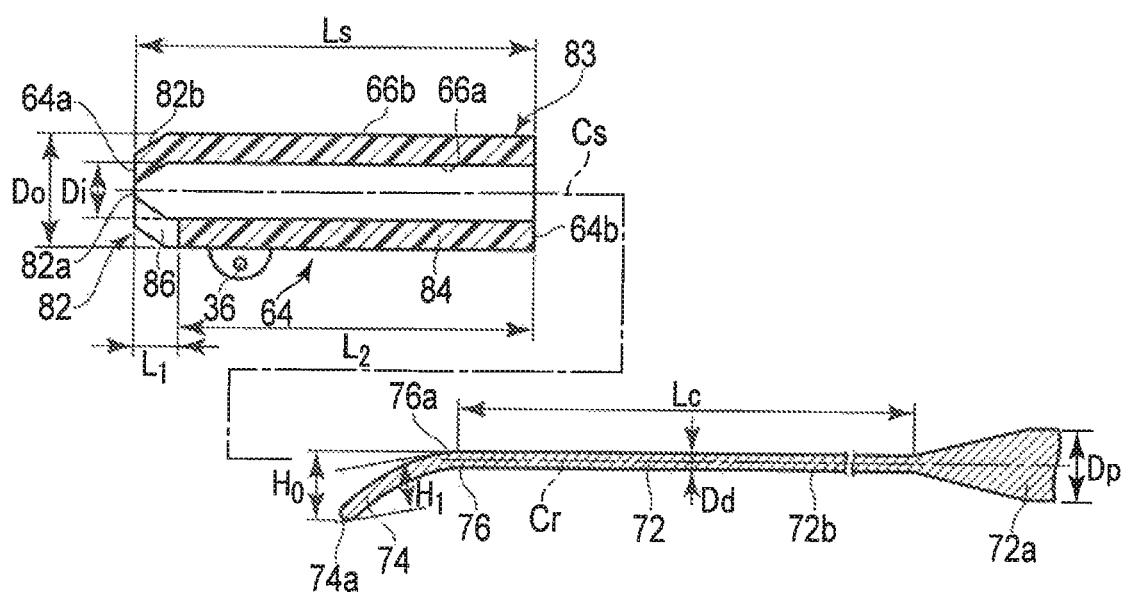
FIG. 4A is a schematic longitudinal sectional view showing a state where the distal end of a waveguide rod put face to face with the proximal end of a second sheath of the treatment instrument of the ultrasonic surgical apparatus according to the first embodiment.

Here, as shown in FIG. 4A, a length along the central axis Cs which is defined by the distal end 64a and a proximal end 64b of the second sheath 64 or defined by the distal portion 82 and the proximal portion 83 that will be described later is Ls, the inside diameter of the inner peripheral surface (inner wall) 66a of the second sheath 64 is Di, and the outside diameter of the outer peripheral surface (sidewall) 66b is Do. In this embodiment, the inside diameter Di of the second sheath 64 is constant from the proximal end 64b of the second sheath 64 to the proximal end 86a of the cutout 86. In the cross section of the second sheath 64, the inner peripheral surface 66a is not limited to a circular shape, and it is also appropriate that the inner peripheral surface 66a be formed into the shape of a long hole. In this case, the aforementioned inside diameter Di of the inner peripheral surface 66a of the second sheath 64 is a size in a major axis direction, and the width in a minor axis direction is formed to be larger than a larger one of the width of the curving portion 74 of the rod 46 and the width of the extension 72. A distance L2 from the proximal end 86a of the cutout 86 to the proximal end 64b of the second sheath 64 is shorter than a length Lc of the constant diameter portion 72b of the extension 72 of the waveguide rod 46.

An outside diameter Dp of the diameter changing portion 72a of the extension 72 of the rod 46 shown in FIG. 4A is larger than the inside diameter Di of the second sheath 64. Thus, even if the diameter decreasing portion 82b is not formed in the distal portion (the distal portion of the sheath 44) 82 of the second sheath 64, the diameter changing portion 72a of the rod 46 can not be passed through the distal end 64a of the second sheath 64.

A maximum height H0 between the constant diameter portion 72b and the distal end 74a of the curving portion 74 in a direction orthogonal to the central axis (longitudinal axis) Cr of the constant diameter portion 72b of the extension 72 of the rod 46 is larger than the inside diameter Di of the second sheath 64. That is, the distance H0 in which the height from the central axis Cr to the distal end 74a of the rod 46 is added to the radius (Dd/2) of the constant diameter portion 72b of the extension 72 of the rod 46 is larger than the inside diameter Di of the second sheath 64. Thus, the rod 46 can not be inserted through the second sheath 64 in a state where the central axis Cr of the rod 46 is kept parallel to the central axis (longitudinal axis) Cs of the second sheath 64.

Here, a top 76a is situated in the vicinity of the curving point 76 and closer to the distal side than the curving point 76. The top 76a is located at a position to contact on or to be closest to the inner peripheral surface of the second sheath 64 on the side opposite to the side where the cutout 86 is formed in a state in which the distal end 74a of the curving portion 74 is disposed on the side where the cutout 86 of the second sheath 64 is formed. Thus, the position of the top 76a changes by the inclination of the central axis Cr of the rod 46 with respect to the central axis Cs of the second sheath 64, as shown in FIG. 4B and FIG. 4C.

Figure 4B:
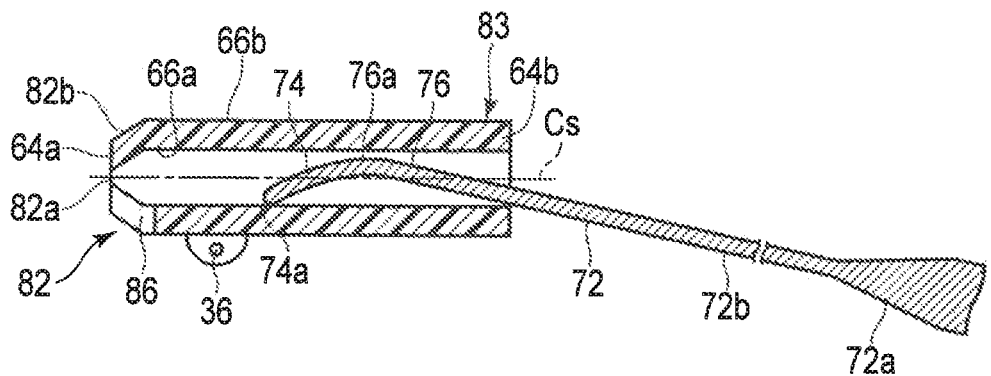
FIG. 4B is a schematic longitudinal sectional view showing a state where a distal portion of the waveguide rod is put into the second sheath from the proximal end of the second sheath, in comparison with the state shown in FIG. 4A.
Figure 4C:
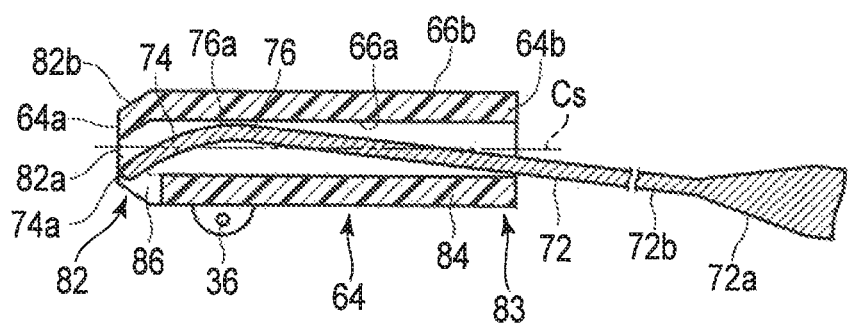
FIG. 4C is a schematic longitudinal sectional view showing a state where the distal end of the waveguide rod reaches a cutout in a distal portion of the second sheath through the inside of the second sheath, in comparison with the state shown in FIG. 4B.

As shown in FIG. 4B, a height (distance) H1 between the top 76a closer to the distal side than the curving point 76 and the distal end 74a of the curving portion 74 is made slightly smaller than the inside diameter Di of the second sheath 64. The inner peripheral surface 66a of the second sheath 64 has the inside diameter Di which is smaller than the distance H0 between the distal end 74a of the curving portion 74 and the extension 72 and which is larger than the distance H1 between the distal end 74a of the curving portion 74 and the top 76a which is a part of the curving portion 74. Thus, the curving portion 74 of the rod 46 can be inserted into the proximal end 64b of the second sheath 64.

Figure 4D:
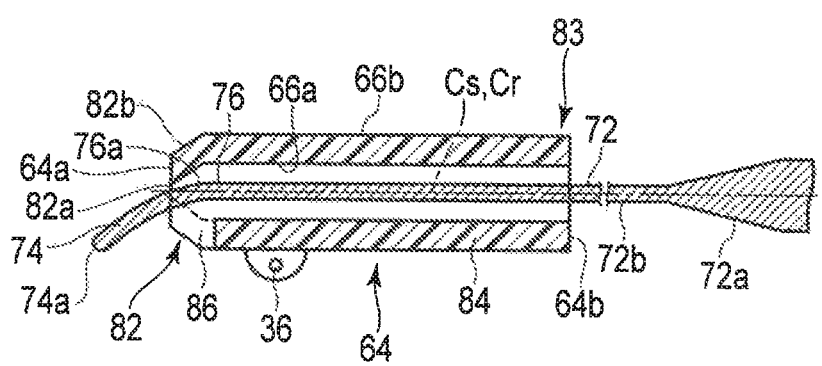
FIG. 4D is a schematic longitudinal sectional view showing a state where the waveguide rod is further inserted into the second sheath, and the waveguide rod is inserted through the second sheath, in comparison with the state shown in FIG. 4C.
Figure 4E:
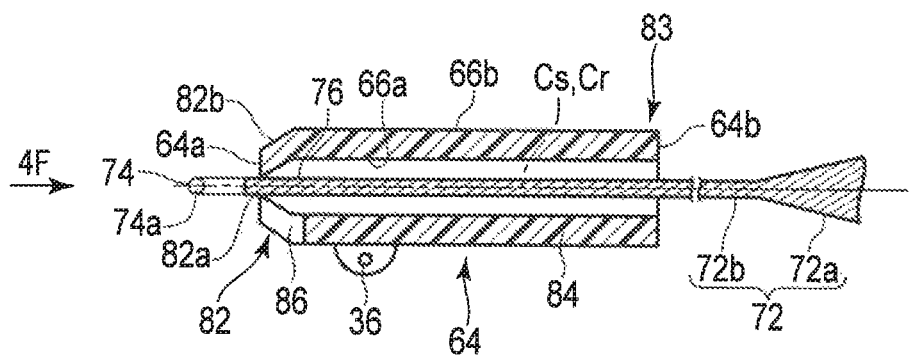
FIG. 4E is a schematic longitudinal sectional view showing a state where the waveguide rod is turned 90° with respect to the second sheath, in comparison with the state shown in FIG. 4D.
Figure 4F:
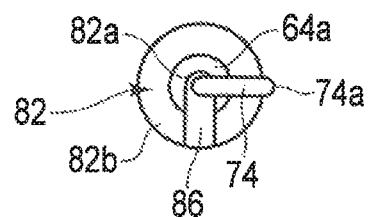
FIG. 4F is a schematic view in which the state shown in FIG. 4E is seen from an arrow 4F direction in FIG. 4E.

The width of the cutout 86 shown in FIG. 4F is formed to be slightly larger than the diameter lid of the constant diameter portion 72b of the extension 72 of the rod 46 and slightly larger than the width of the octagon of the curving portion 74.

Figure 2B:
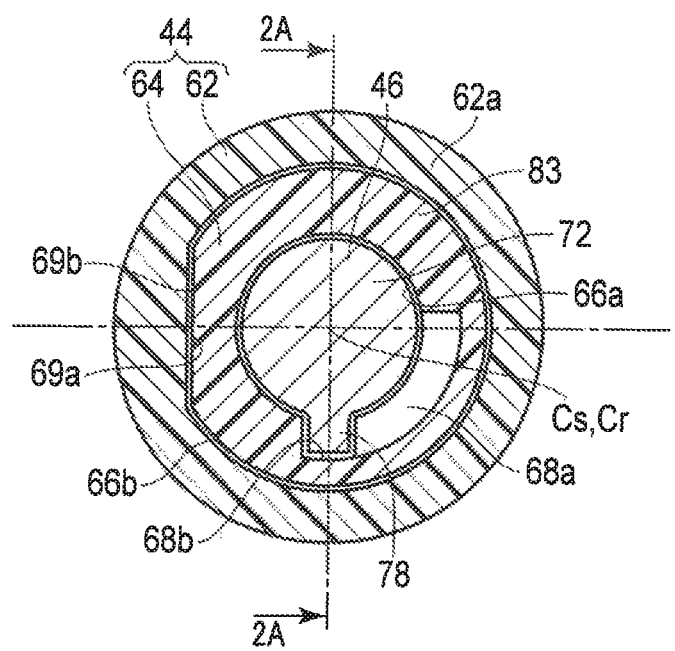
FIG. 2B is a schematic cross sectional view taken along the line 2B-2B in FIG. 2A.
Figure 2C:
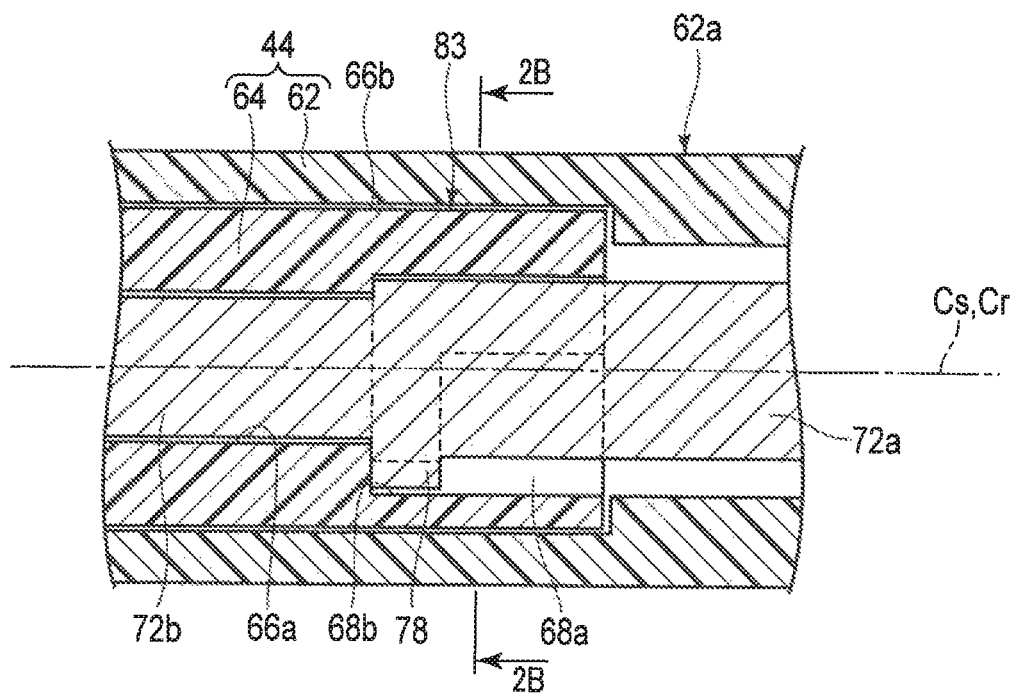
FIG. 2C is a schematic longitudinal sectional view taken along the line 2A-2A in FIG. 2B, showing a position indicated by a reference mark 20 in FIG. 2A in an enlarged form.

As shown in FIG. 2B and FIG. 2C, a step is formed between the distal end of the diameter changing portion 72a of the extension 72 of the waveguide rod 46 and the proximal end of the constant diameter portion 72b. A step is formed in the proximal portion 83 of the second sheath 64 along a later-described lock groove 68b. Thus, the position of the distal end of the diameter changing portion 72a with respect to the second sheath 64, that is, the position of the rod 46 with respect to the second sheath 64 can be defined. The position of the distal end of the diameter changing portion 72a which is brought into collision with the lock groove 68b of the second sheath 64 in this instance corresponds to a node position of vibration when the vibration is transmitted to the rod 46 from the ultrasonic transducer unit 12.

A protruding portion 78 which diametrically outwardly protrudes with respect to the central axis Cr is formed in a distal portion of the diameter changing portion 72a of the extension 72 of the waveguide rod 45. A guide groove 68a and the lock groove 68b are formed in the proximal portion 83 of the second sheath 64. The guide groove 68a is formed into an arc shape within a suitable range, for example, within a range of about 90°. Thus, the guide groove 68a can guide the protruding portion 78 of the waveguide rod 46 toward the lock groove 68b while turning the protruding portion 78 around the central axes Cs and Cr. Therefore, the second sheath 64 and the rod 46 are relatively turnable within a predetermined range in a state where the central axis Cr of the second sheath 64 is aligned with the central axis (longitudinal axis) Cr of the rod 46. The lock groove 68b is formed at the lower end of the guide groove 68a in FIG. 2B and FIG. 2C. The lock groove 68b is formed on the distal side along the central axes Cs and Cr with respect to the guide groove 68a. Further, the lock groove 68b can receive the protruding portion 78 of the rod 46, but is formed so that the lock groove 68b can not turn when receiving the protruding portion 78. Therefore, as shown in FIG. 1 and FIG. 2A, the curving portion 74 of the waveguide rod 46 is supported in a state where its direction is determined with respect to the distal portion 82 of the second sheath 64. That is, the guide groove 58a and the lock groove 68b of the second sheath 64 and the protruding portion 78 of the rod 46 form a positioning mechanism which positions in a state where the distal end 74a of the curving portion 74 faces in a predetermined direction with respect to the opening 82a of the second sheath 64.

The guide groove 68a of the second sheath 64 shown in FIG. 2B and FIG. 2C is formed within a range of, for example, about 90°, As long as the protruding portion 78 of the rod 46 is locked to the lock groove 68b of the second sheath 64, the curving portion 74 of the second sheath 64 has only to be able to be held at a position skewed with respect to a state where the rod 46 is inserted through the second sheath 64.

As shown in FIG. 2B, a flat portion 69a having, for example, a D-shaped cross section is provided in the inner peripheral surface of the distal portion 62a of the first sheath 62. Similarly, a flat portion 69b having, for example, a D-shaped cross section is provided in the outer peripheral surface of the proximal portion 83 of the second sheath 64. If the distal portion 62a of the first sheath 52 and the outer peripheral surface of the proximal portion 83 of the second sheath 64 are fitted together, the flat portions 69a and 69b face each other. Thus, in the first and second sheaths 62 and 64, a rotation preventing mechanism which prevents the first and second sheaths 62 and 64 from rotating with respect to each other is formed.

Furthermore, the first and second sheaths 62 and 64, particularly, the first sheath 64 is supported in a state Where its direction is determined around the central axis Cs with respect to the housing 42. The aforementioned the flat portion can be suitably used for this structure. Moreover, the movement of the sheath 44 with respect to the housing 42 along the central axis Cs can also be prevented by suitably using a publicly known mechanism. In this way, the sheath 44 through which the rod 46 is inserted is supported in a predetermined state with respect to the housing 42, so that the treatment instrument main body 32 is formed. In this instance, the curving portion 74 of the waveguide rod 46 inserted through the first sheath 62 always faces in a constant direction with respect to the housing 42. Further, one end of the shaft 36 is supported on the second sheath 64.

The clamp arm 34 has a rod-shaped member 92 having a pair of arm members 92a and 92b split in two ways. The clamp arm 34 is coated with an electrically insulating resin material or the like. The distal portion 82 of the second sheath 64 is inserted between these arm members 92a and 92b, and the inner peripheral surfaces of the pair of arm members 92a and 92b are coupled to the outer side of the second sheath 64 via the shaft 36, whereby the clamp arm 34 is pivotally supported swingably (turnably) on the treatment instrument main body 32.

A second finger putting portion 94 which pairs with the first finger putting portion 52 provided in the treatment instrument main body 32 is formed in a proximal portion of the clamp arm 34. The second finger putting portion 94 is formed into a shape appropriate to dispose, for example, the thumb of the surgeon. Then, for example, the surgeon relatively moves the fingers (e.g. the ring finger and the little finger) disposed on the first finger putting portion 52 and the finger (e.g. the thumb) disposed on the second finger putting portion 94, and the clamp arm 34 can thereby swing on the shaft. 36.

A seat 96 having a crooked portion 96a which avoids interference with the second sheath 64 (the sheath 44) when the clamp arm 34 is swung is provided on the distal side of the clamp arm 34 which crosses the treatment instrument main body 32 via the shaft 36. The jaw 98 is provided on the seat 96. The jaw 98 is formed into a shape that can receive the curving portion 74 of the rod 46 to obtain grasping force for the living tissue. Thus, it is appropriate that the jaw 98 curve in the same manner as the curving portion 74 of the rod 46.

As shown in FIG. 1 and FIG. 2A, the jaw 98 is supported on the seat 96. The jaw 98 is movable between a closing state to contact on the curving portion 74 of the rod 45 and an open state to separate from the curving portion 74 of the rod 46, in response to the swinging of the clamp arm 34. The jaw 98 has a function as the electrically conductive second electrode portion in accordance with the curving portion 74 of the rod 46 which functions as the first electrode portion. Naturally, the shape of the jaw 98 is not limited to the example shown in the drawing.

Thus, a region where the jaw 98 and the curving portion 74 of the rod 46 move to be able to come in and out of contact (be able to open and close) constitutes a treatment portion 100 which is a region effective in performing various treatments of the living tissue, such as cutting, resection, or coagulation.

As shown in FIG. 3, the jaw 98 includes the pair of inclined surfaces 98a, and a press pad 98b formed in a bottom portion between the pair of inclined surfaces 98a. The pair of inclined surfaces 98a are inclined at a predetermined angle to a surface facing the curving portion 74 of the rod 46, from the edges of the inclined surfaces 98a toward the central part. The pair of inclined surfaces 98a have electric conductivity which permits the passage of the frequency electric current output from the output controller 14, and are formed to have a space between the pair of inclined surfaces 98a and the curving portion 74 of the rod 46 as the first electrode portion even when the jaw 98 is brought closest to the curving portion 74 of the rod 46. The press pad 98b is made of an electrically insulating, heat-resistant, and abrasion-resistant resin material such as a PTFE material. The press pad 98b abuts on the curving portion 74 to the extent that pressure can he applied to the curving portion 74 when the jaw 98 is brought closest to the curving portion 74 of the rod 46.

Now, effects of the treatment instrument 16 according to this embodiment are described with reference to FIG. 4A to FIG. 4F, and FIG. 5. In the example mainly described here, the waveguide rod 46 is inserted through the second sheath 64 to form the treatment instrument main body 32.

As shown in FIG. 4A, the distal end 74a of the rod 46 is put face to face with the proximal end 64b of the second sheath 64. At this point, the height H0 of the rod 46 is greater than the inside diameter Di of the second sheath 64. Therefore, the second sheath 64 can not be inserted through the rod 46 in a state where the central axis Cs of the second sheath 64 is aligned with or kept parallel to the central axis Cr of the rod 46.

As shown in FIG. 4B, the central axis Cr of the rod 46 is inclined with respect to the central axis Cs of the second sheath 64. The height Hi between the top 76a closer to the distal side than the curving point 76 and the distal end 74a of the curving portion 74 is made slightly smaller than the inside diameter Di of the second sheath 64. Further, the curving point 76 of the rod 46 is disposed on the side opposite to the side where the cutout 86 of the second sheath 64 is formed, the distal end 74a of the rod 46 is disposed on the side where the cutout 86 is formed and then inserted toward the distal end 64a from the proximal end 64b of the second sheath 64. At this point, the rod 46 is inserted while the inclination of the central axis Cr of the rod 46 is gradually decreased with respect to the central axis Cs of the second sheath 64.

When the rod. 46 is inserted into the second sheath 64, two points of the distal end 74a and the top 76a of the curving portion 74 of the rod 46 and the constant diameter portion 72b of the extension 72 contact on the second sheath 64, but remaining one point does not contact at the same time. For example, as shown in FIG. 4B, the distal end 74a of the curving portion 74 of the rod 46 contacts on the inner peripheral surface of the second sheath 64 on the side where the cutout 86 is formed. The constant diameter portion 72b of the extension 72 of the rod 46 contacts the side of the proximal end 64b of the second sheath 64 where the cutout 86 is formed. At this point, the top 76a of the curving portion 74 is close to but away from the inner peripheral surface of the second sheath 64 on the side opposite to the side where the cutout 86 is formed. That is, when two points of the distal end 74a of the curving portion 74 of the rod. 46 and the constant diameter portion 72b of the extension 72 abut on the second sheath 64, the top 76a of the curving portion 74 is away from the inner peripheral surface of the second sheath 64.

As shown in FIG. 4C, the top 76a of the curving portion 74 of the rod 46 abuts on the inner peripheral surface of the second sheath 64 on the side opposite to the side where the cutout 86 is formed. The constant diameter portion 72b of the extension 72 of the rod 46 contacts the side of the proximal end 64b of the second sheath 64 where the cutout 86 is formed. At this point, the distal end 74a of the curving portion 74 of the rod 46 is located in the cutout 86. That is, when two points of the top 76a of the curving portion 74 and the constant diameter portion 72b of the extension 72 abut on the second sheath 64, the distal end 74a of the curving portion 74 of the rod 46 is located in the cutout 86, and is away from the inner peripheral surface of the second sheath 64. When the rod 46 is moved with respect to the second sheath 64 from the state shown in FIG. 4B to the state shown in FIG. 4C, neither the second sheath 64 nor the curving portion 74 of the rod 46 needs to be elastically deformed. Thus, when the rod 46 is inserted into the second sheath 64, it is possible to prevent a load from being applied to the second sheath 64 from the rod 46.

As shown in FIG. 4D, in a state where the curving portion 74 of the rod 46 is disposed in the cutout 86, the central axis Cr of the rod 46 is made parallel to the central axis Cs of the second sheath 64. That is, if the curving portion 74 of the rod 46 is disposed in the cutout 86, the central axis Cr of the rod 46 can be aligned with the central axis Cs of the second sheath 64. At this point, the rod 46 is inserted through the second sheath 64. Moreover, the rod 46 can not be pulled out of the second sheath 64 in a state where the central axis Cs of the second sheath 64 is aligned with or kept parallel to the central axis Cr of the rod 46.

Furthermore, as shown in FIG. 2B, FIG. 2C, FIG. 4E, and FIG. 4F, in a state where the central axis Cs of the second sheath 64 is aligned with the central axis Cr of the rod 46, the protruding portion 78 of the extension 72 of the rod 46 is disposed in the guide groove 68a formed in the proximal portion 83 of the second sheath 64. In this state, the rod 46 is turned, for example, about 90° with respect to the second sheath 64. That is, the protruding portion 78 of the extension 72 of the rod 46 is disposed in the lock groove 68b from the guide groove 68a formed in the proximal portion 83 of the second sheath 64. Thus, the second sheath 64 holds the curving portion 74 of the rod 46 at a position skewed with respect to a direction in which the curving portion 74 is passed through the cutout 86 in a state where the curving portion 74 of the rod 46 protrudes from the opening 82a of the second sheath 64. At this point, because the direction of the curving portion 74 of the rod 46 is 90° different from the cutout 86 of the second sheath 64, the rod 46 is prevented from coming off the second sheath 64.

Figure 5:
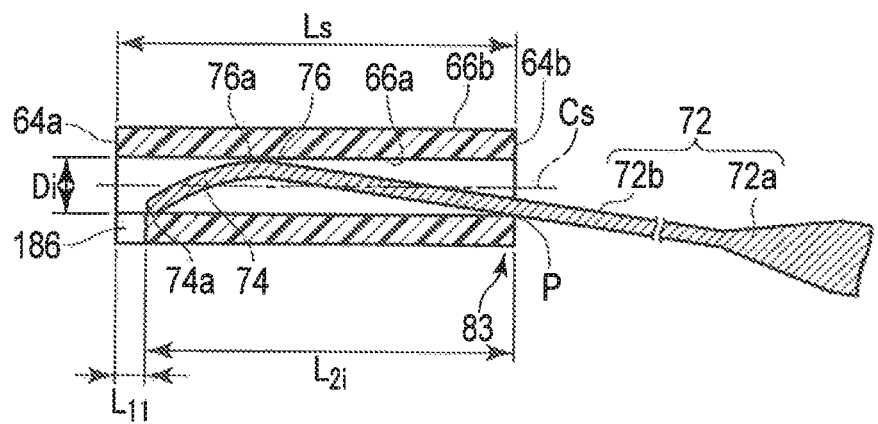
FIG. 5 is a schematic longitudinal sectional view showing an undesirable example of a second sheath through which the waveguide rod can not be inserted from a proximal end to a distal end of the second sheath.

In addition, FIG. 5 shows an undesirable example of a second sheath 164 through which the rod 46 shown in FIG. 4A to FIG. 4F can not be inserted.

The distance between the distal end 64a of the second sheath 164 and the proximal end of a cutout 186 shown in FIG. 5 is L11, and distance between the proximal end of the cutout 86 and the proximal end 64b of the second sheath 164 is L21. That is, Ls=L11+L21. The length L11 of the cutout 186 with respect to the distal end 64a of the second sheath 164 is smaller than the length L1 of the cutout 86 with respect to the distal end 64a of the second sheath 64 shown in FIG. 4A to FIG. 4E. That is, the length L21 shown in FIG. 5 is greater than the length L2 of the second sheath 64 shown in FIG. 4A to FIG. 4E. The second sheath 164 shown in FIG. 5 and the second sheath 64 shown in FIG. 4A to FIG. 4E are the same other than the length of the cutout 86.

When the rod 46 is inserted through the second sheath 164 shown in FIG. 5, three points of the distal end 74a and the top 76a of the curving portion 74 of the rod 46 and the constant diameter portion 72b of the extension 72 abut on the inner Peripheral surface of the second sheath 164 if the rod 46 shown in FIG. 4A to FIG. 4E is used. At this point, even if an attempt is made to align the central axis Cr of the rod 46 with the central axis Cs of the second sheath 164, it is necessary to apply a load to the second sheath 164 and the rod 46 to elastically deform the second sheath 164 and the rod 46.

A part (which is a movable contact) of the constant diameter portion 72b of the rod 46 which contacts the proximal end 64b of the second sheath 164 is P. When the rod 46 is disposed the second sheath 164, a component, which is orthogonal to the central axis Cs, of the distance between the top 76a and the contact P of the constant diameter portion 72b corresponds to the inside diameter Di of the second sheath 164. At this point, the distance between the distal end 74a of the rod 46 and the contact P of the constant diameter portion 72b is shorter than L21.

As shown in FIG. 4C, for the distal end 74a of the rod 46 to be disposed in the cutout 86, the distance between the distal end 74a of the rod 46 and the contact P needs to be greater than the distance L2 between the proximal end 86a of the cutout 85 and the proximal end 64b of the second sheath 64 when the top 76a and the contact P abut on the inner peripheral surface of the second sheath 64.

The distance L2 (=Ls−L1) between the proximal end of the cutout 86 of the second sheath 64 and the proximal end 64b of the second sheath 64 according to this embodiment is formed to be shorter than the distance between the distal end 74a of the rod 46 and the contact P, for example, when the top 76a of the rod 46 and the contact P of the constant diameter portion 72b abut on the inner peripheral surface of the second sheath 64. Therefore, the second sheath 64 shown in FIG. 4A to FIG. 4E permits the rod 46 to be inserted through the second sheath 64 without interference if the length L1 of the cutout 86 is suitably great in accordance with the shape of the rod 46. That is, the cutout 86 cuts out from the distal end 64a of the second sheath 64 to a position of the second sheath 64 in which a distal end 74a of the curving portion 74 of the rod 46 is configured to be disposed. More specifically, the cutout 86 cuts out from the distal end 64a of the sheath 64 to a position of the sheath 64 in which the distal end 74a of the curving portion 74 of the rod 46 is configured to be disposed, when the extension 72 of the rod 46 contacts the proximal end 64a of the sheath 64 and when a top 76a as a part of the curving portion 74 of the rod 46 contacts the inner peripheral surface 66a of the sheath 64.

As shown in FIG. 4A, the inside diameter of the first sheath 62 is larger than the outside diameter Dp of the diameter changing portion 72a of the extension 72 of the waveguide rod 46 protruding toward the proximal side from the proximal end 64b of the second sheath 64. Thus, the diameter changing portion 72a of the waveguide rod 46 is inserted from the distal end to the proximal end of the first sheath 62. Then, as shown in FIG. 2C, the distal portion 62a of the first sheath 62 is fixed to the proximal portion 83 of the second sheath 64 in a state where rotation is prevented. Further, in a state where the rod 46 is positioned and disposed with respect to the sheath 44, the sheath 44 is disposed in the housing 42 in a predetermined direction to form the treatment instrument main body 32.

Then, as shown in FIG. 1, the shaft 36 is attached to the part between the second sheath 64 of the treatment instrument main body 32 and the pair of arm members 92a and 92b of the clamp arm 34 to form the treatment instrument 16.

When the living tissue is treated with this treatment instrument 16, the ultrasonic transducer unit 12 is properly attached to the proximal end of the housing 42 of the treatment instrument 16. In this instance, because the sheath 44 and the rod 46 are prevented from rotating with respect to the housing 42, the direction of the curving portion 74 of the rod 46 with respect to the jaw 98 is maintained even if the ultrasonic transducer unit 12 is connected to the treatment instrument 16.

The surgeon opens and closes the jaw 98 with respect to the curving portion 74 of the rod 46 (i.e. opens and closes the treatment portion 100) by the operation of the first and second finger putting portions 52 and 94 which are operation portions, and nips the living tissue between the curving portion 74 of the rod 46 and the pad 98b of the jaw 98.

In this state, if the button switch 54 is pressed, the bipolar type high-frequency output is performed in the seal mode for the living tissue between the curving portion 74 of the rod 46 and the inclined surfaces 98a of the jaw 98, and the nipped living tissue is coagulated. If the living tissue is a blood vessel, the blood vessel is sealed.

If the button switch 56 is pressed, the ultrasonic output and the bipolar type high-frequency output are simultaneously performed in the seal-and-cut mode. That is, the bipolar type high-frequency output is performed in the seal mode for the living tissue between the curving portion 74 of the rod 46 and the press pad 98b of the law 98, and the living tissue between the curving portion 74 of the rod 46 and the press pad 98b the jaw 98 is also cut open by the ultrasonic vibration. It is therefore possible to coagulate and cut open the living tissue at the same time. If the living tissue is a blood vessel, the blood vessel is sealed and cut open at the same time.

As described above, the following can be said according to the treatment instrument (medical instrument) 16 in this embodiment.

The second sheath 64 is formed by a single member, and the waveguide rod 45 having the curving portion 74 in the distal portion can be inserted from the proximal end of the second sheath 64 toward its distal end, in this instance, it is possible to insert the waveguide rod 46 through the second sheath 64 without interference by forming the cutout 86 in the distal portion 82 of the second sheath 64. Therefore, because of the presence of the cutout 86 of the second sheath 64, the second sheath 64 does not need to be increased in diameter or formed as divided bodies, and the waveguide rod 46 having the curving portion 74 can be inserted through the second sheath 64. That is, according to this embodiment, it is possible to provide the treatment instrument (medical instrument) 16 having the sheath 44 wherein the increase in the outside diameter of the distal portion 82 suppressed; nevertheless, a state where the waveguide rod 46 is inserted can be obtained. Moreover, the second sheath 64 is formed by a single member, so that even if a load is applied to the second sheath 64 from, for example, a living tissue, there is no unfitting of fitting portions because no fitting portions are present. That is, even when a load is applied to the second sheath 64, it is possible to prevent the effect of the unfitting of components or the like.

The diameter decreasing portion 82b is formed in the distal portion 82 of the second sheath 64. Thus, when the curving portion 74 of the rod 46 is viewed through the distal portion $2 of the second sheath 64, it is difficult for the distal portion 82 of the second sheath 64 to interfere. Therefore, visibility of the curving portion 74 of the rod 46 can be maintained because the distal portion 82 of the second sheath 64 has the diameter decreasing portion 82b. The distal portion 82 of the second sheath 64 is formed as thinly as possible, so that insertability into a narrow part can be higher when the distal end 64a of the second sheath 54 is inserted into the narrow part.

Now, the second embodiment is described with reference to FIG. 6A and FIG. 6B. This embodiment is a modification of the first embodiment, and the same reference numbers are given as much as possible to the same members as the members described in the first embodiment, or the members having the same functions, and detailed descriptions are omitted.

As shown in. FIG. 6A and. FIG. 6B, here, the cutout 86 of the second sheath 64 is formed into a depressed shape such as a flute shape on the inner peripheral surface side of the second sheath 64. That is, this cutout 86 does not appear in the outer peripheral surface 66b of the second sheath 64.

Although the cutout 86 is formed in the distal portion 82 of the second sheath 64 as above, the waveguide rod 46 can be inserted through the second sheath 64 without interference, as has been described in the first embodiment. Therefore, because of the presence of the cutout 86 of the second sheath 64, the second sheath 64 does not need to be increased in diameter or formed as divided bodies, and the rod 46 having the curving portion 74 can be inserted through the second sheath 64.

Now, the third embodiment is described with reference to FIG. 7. This embodiment is a modification of the first and second embodiments, and the same reference numbers are given as much as possible to the same members as the members described in the first and second embodiments, or the members having the same functions, and detailed descriptions are omitted.

Figure 7:
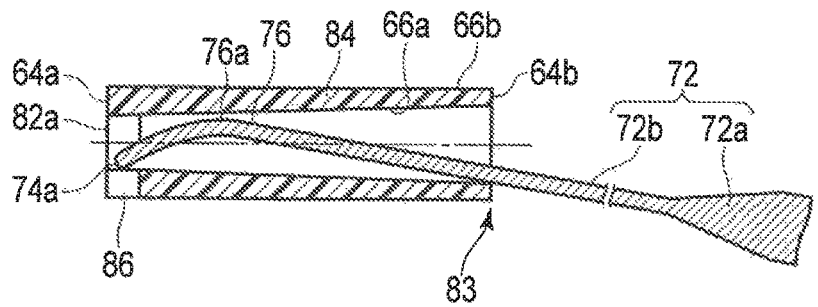
FIG. 7 is a schematic longitudinal sectional view showing the states of the second sheath and the waveguide rod in the case where the waveguide rod is to be inserted through the second sheath according to the third embodiment.

As shown in FIG. 7, the inside diameter Di of the second sheath 64 is formed to be smaller on the distal side and larger on the proximal side. In FIG. 7, the length L1 from the distal end 64a of the second sheath 64 to the proximal end 86a of the cutout 86 is different, but the shape of the cutout 86 is formed to be similar to that in the first embodiment. Naturally, the shape of the cutout 86 may be formed to be the flute shape described in the second embodiment.

Now, the fourth embodiment is described with reference to FIG. 8. This embodiment is a modification of the first to third embodiments, and the same reference numbers are given as much as possible to the same members as the members described in the first to third embodiments, or the members having the same functions, and detailed descriptions are omitted.

Here, a cutout (proximal-side cutout) 87 is formed not in the distal portion 82 of the second sheath 64 but in the proximal portion 83. Here, the cutout 87 passes through from an inner peripheral surface 66a of the second sheath 64 to the outer peripheral surface 66b which is diametrically outwardly located with respect to the central axis Cs.

The second sheath 64 is formed by a single member, and the waveguide rod 46 having the curving portion 74 in the distal portion can be inserted from the proximal end of the second sheath 64 toward its distal end. In this instance, it is possible to insert the waveguide rod 46 through the second sheath 64 without interference by forming the cutout. 87 in the proximal portion 83 of the second sheath 64. Therefore, because of the presence of the cutout 87 of the second sheath 64, the second sheath 64 does not need to be increased in diameter or formed as divided bodies, and the waveguide rod 46 having the curving portion 74 can be inserted through the second sheath 64.

Figure 6A:
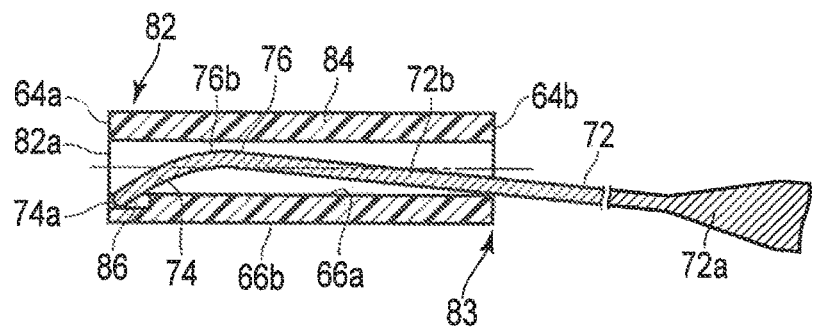
FIG. 6A is a schematic longitudinal sectional view showing the states of the second sheath and tae-waveguide rod in the case where the waveguide rod is to be inserted through the second sheath according to the second embodiment.
Figure 6B:
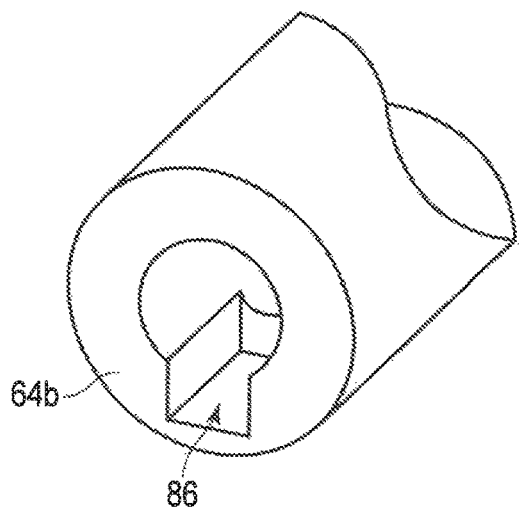
FIG. 6B is a schematic perspective view showing a distal portion of the second sheath according to the second embodiment.
Figure 8:
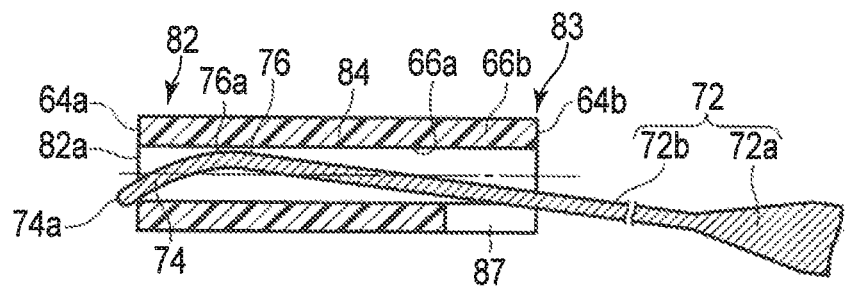
FIG. 8 is a schematic longitudinal sectional view showing the states of the second sheath and the waveguide rod in the case where the waveguide rod is to be inserted through the second sheath according to the fourth embodiment.

The shape of the cutout 87 is not limited to the shape shown in FIG. 8, and may be the flute shape shown in FIG. 6A and FIG. 6B. Moreover, the inside diameter Di of the second sheath 64 may be formed to be smaller on the distal side and larger on the proximal side, as shown in FIG. 7.

Now, the fifth embodiment is described with reference to FIG. 9. This embodiment is a modification of the first to fourth embodiments, and the same reference numbers are given as much as possible to the same members as the members described in the firs to fourth embodiments, or the members having the same functions, and detailed descriptions are omitted.

In the example here, the distal-side cutout 86 is formed in the distal portion 82 of the second sheath 64, and the proximal-side cutout 87 is formed in the proximal portion 83. That is, in the second sheath 64 according to the present embodiment, the cutouts 86 and 87 are formed in both the distal portion 82 and the proximal portion 83, respectively. In this case, as shown in FIG. 9, both the cutouts 86 and 87 are formed in the same direction on the lower side of the central axis Cs in a longitudinal section of the second sheath 64 including the central axis Cs.

The second sheath 64 is formed by a single member, and the waveguide rod 46 having the curving portion 74 in the distal portion can be inserted from the proximal end of the second sheath 64 toward its distal end. In this instance, it is possible to insert the waveguide rod 46 through the second sheath 64 without interference by forming the cutout 86 in the distal portion 82 of the second sheath 64 and forming the cutout 87 in the proximal portion 83. Therefore, because of the presence of the cutouts 86 and 87 of the second sheath 64, the second sheath 64 does not need to be increased in diameter or formed as divided bodies, and the waveguide rod 46 having the curving portion 74 can be inserted through the second sheath 64.

Figure 9:
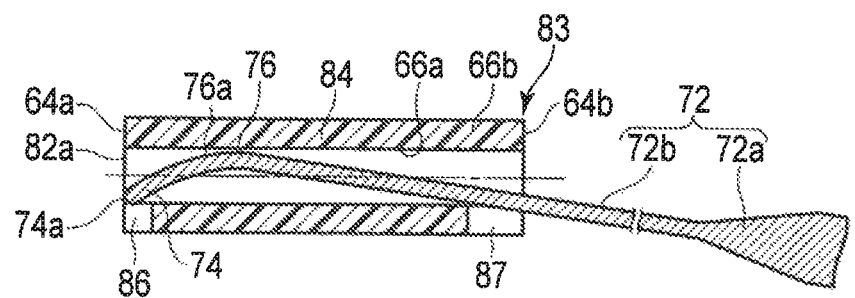
FIG. 9 is a schematic longitudinal sectional view showing the states of the second sheath and the waveguide rod in the case where the waveguide rod is to be inserted through the second sheath according to the fifth embodiment.

The shapes of the cutouts 86 and 87 are not limited to the shapes shown in FIG. 9, and may be the flute shape shown in FIG. 6A and FIG. 6B. Further, the cutout 86 of the distal portion 82 may be different in shape from the cutout 87 of the proximal portion 83. Moreover, the inside diameter Di of the second sheath 64 may be formed to be smaller on the distal side and larger on the proximal side.

Now, the sixth embodiment is described with reference to FIG. 10A and FIG. 10B. This embodiment is a modification of the first to fifth embodiments, and the same reference numbers are given as much as possible to the same members as the members described in the first to fifth embodiments, or the members having the same functions, and detailed descriptions are omitted.

Figure 10A:
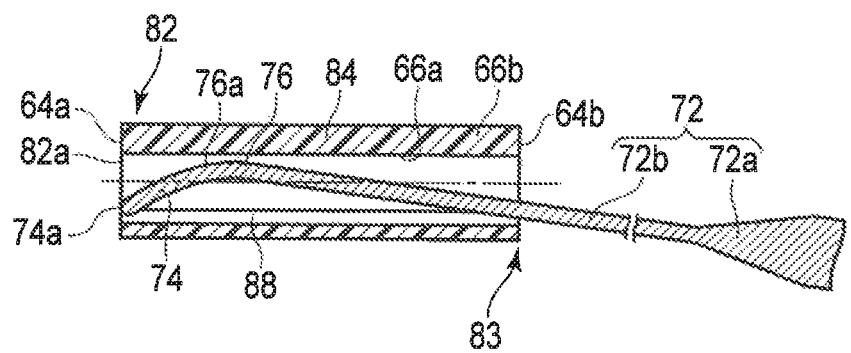
FIG. 10A is a schematic longitudinal sectional view showing the states of the second sheath and the waveguide rod in the case where the waveguide rod is to be inserted through the second sheath according to the sixth embodiment.
Figure 10B:
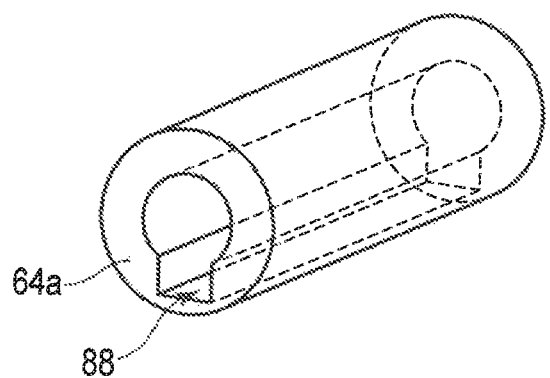
FIG. 10B is a schematic perspective view showing the second sheath according to the sixth embodiment.

As shown in FIG. 10A and FIG. 10B, a key groove is formed as a cutout 88 in the inner peripheral surface of the second sheath 64 to continuously extend over the entire length between the distal end 64a and the proximal end 64b of the second sheath 64. That is, the cutout 88 is formed into a depressed shape between the inner peripheral surface 66a and the outer peripheral surface 66b of the second sheath 64.

The second sheath 64 is formed by a single member, and the waveguide rod 46 having the curving portion 74 in the distal portion can be inserted from the proximal end of the second sheath 64 toward its distal end. In this instance, it is possible to insert the waveguide rod 46 through the second sheath 64 without interference by forming the cutout 88 in the second sheath 64. Therefore, because of the presence of the cutout 88 of the second sheath 64, the second sheath 64 does not need to be increased in diameter or formed as divided bodies, and the waveguide rod 46 having the curving portion 74 can be inserted through the second sheath 64.

When the same waveguide rod as the waveguide rod 46 described in the first to fifth embodiments is used, the inside diameter Di of the second sheath 64 can be smaller than that of the second sheath 64 described in the first to fifth embodiments because of the key-groove shaped cutout 88.

Moreover, as shown in FIG. 7, the inside diameter Di of the second sheath 64 may be formed to be smaller on the distal side and larger on the proximal side.

Although an outside diameter Do of the second sheath 64 is constant from the distal end 64a to the proximal end 64b in the illustration according to the second to sixth embodiments, the diameter decreasing portion 82b may naturally be formed in the distal portion 82 as has been described in the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A medical instrument comprising:
   a rod including an extension which extends along a longitudinal axis, and a curving portion which is formed on a distal side of the extension and which is curved with respect to the longitudinal axis;

a sheath including an inner peripheral surface and a cutout which is formed in at least one of a distal portion and a proximal portion of the sheath, the sheath being configured to insert the rod along a central axis extending and defined from the distal portion to the proximal portion and to protrude the curving portion from an opening of the inner peripheral surface in the distal portion; and a clamp arm which is coupled to the sheath via a shaft and which includes a jaw that receives the curving portion, wherein:

the inner peripheral surface of the sheath has an inside diameter smaller than a distance between a distal end of the curving portion in a direction orthogonal to the longitudinal axis and the extension, and larger than a distance between the distal end of the curving portion in a direction orthogonal to the central axis of the sheath and a position where the curving portion contacts the inner peripheral surface in a state where the curving portion contacts the inner peripheral surface, and in the case where the cutout of the sheath is in the distal portion of the sheath, the cutout cuts out from a distal end of the sheath to a position of the sheath in which a distal end of the curving portion of the rod is configured to be disposed, when the extension of the rod contacts a proximal end of the sheath and when the curving portion of the rod contacts an inner peripheral surface of the sheath.

2. The medical instrument according to claim 1, wherein in the case where the cutout is in the distal portion of the sheath, the cutout cuts out from a distal end of the sheath to a position of the sheath in which a distal end of the curving portion of the rod is configured to be disposed.

3. The medical instrument according to claim 1, wherein in the case where the cutout is in the proximal portion of the sheath, the cutout cuts out from a proximal end of the sheath to a position of the sheath in which a distal end of the curving portion of the rod is configured to be disposed on a distal side of the opening along the central axis, when the extension of the rod contacts the distal end of the cutout and when a part of the curving portion of the rod contacts an inner peripheral surface of the sheath.

4. The medical instrument according to claim 1, wherein the cutout passes through from the inner peripheral surface of the sheath to an outer peripheral surface of the sheath which is diametrically outwardly located with respect to the central axis.

5. The medical instrument according to claim 1, wherein the cutout is a depression between the inner peripheral surface of the sheath and an outer peripheral surface of the sheath.

6. The medical instrument according to claim 1, wherein the cutout is formed by cutting out a part of the inner peripheral surface of the sheath.

7. The medical instrument according to claim 1, wherein the cutout continuously extends between a distal end and a proximal end of the sheath.

8. The medical instrument according to claim 1, wherein the extension is located distal to the opening of the sheath along the central axis.

9. The medical instrument according to claim 1, wherein the sheath and the rod are relatively turnable within a predetermined range in a state where the central axis of the sheath is aligned with the longitudinal axis of the rod.

10. The medical instrument according to claim 1, wherein the sheath is configured to hold the curving portion of the rod at a position skewed with respect to a direction in which the curving portion is passed through the cutout in a state where the curving portion of the rod extends from the opening.

11. The medical instrument according to claim 1, wherein the sheath and the rod form a positioning mechanism which positions in a state where the distal end of the curving portion faces in a predetermined direction with respect to the opening of the sheath.

12. The medical instrument according to claim 1, wherein in the case where the cutout is in the distal portion of the sheath, the cutout does not interfere with the curving portion of the rod when the distal end of the curving portion of the rod is rotated around the longitudinal axis.

13. An ultrasonic surgical apparatus comprising:
the medical instrument according to claim 1; and
an ultrasonic transducer unit configured to transmit vibration to the rod of the medical instrument.

14. The medical instrument according to claim 1, wherein the inside diameter of the inner peripheral surface of the sheath is smaller than a distance in which a height from the longitudinal axis to the distal end of the curving portion in a direction orthogonal to the longitudinal axis is added to the radius of the extension.

* * * * *